US012551255B2

(12) United States Patent
Vogt et al.

(10) Patent No.: US 12,551,255 B2
(45) Date of Patent: Feb. 17, 2026

(54) DEVICE AND METHOD FOR PROVIDING BONE CEMENT PASTE

(71) Applicant: Heraeus Medical GmbH, Wehrheim (DE)

(72) Inventors: Sebastian Vogt, Wehrheim (DE); Thomas Kluge, Wehrheim (DE)

(73) Assignee: Heraeus Medical GmbH, Wehrheim (DE)

( * ) Notice: Subject to any disclaimer, the term of this patent is extended or adjusted under 35 U.S.C. 154(b) by 334 days.

(21) Appl. No.: 18/192,774

(22) Filed: Mar. 30, 2023

(65) Prior Publication Data

US 2023/0310048 A1 Oct. 5, 2023

(30) Foreign Application Priority Data

Apr. 4, 2022 (EP) .................................... 22166434

(51) Int. Cl.
*A61B 17/88* (2006.01)

(52) U.S. Cl.
CPC .. *A61B 17/8825* (2013.01); *A61B 2017/8838* (2013.01)

(58) Field of Classification Search
CPC ............ A61B 17/8802; A61B 17/8825; A61B 17/8833; A61B 2017/8838
See application file for complete search history.

(56) References Cited

U.S. PATENT DOCUMENTS 4,671,263 A 6/1987 Draenert
4,973,168 A 11/1990 Chan
5,100,241 A 3/1992 Chan
5,344,232 A 9/1994 Nelson et al.
5,551,778 A * 9/1996 Hauke .................. B01F 35/187 366/139
5,586,821 A 12/1996 Bonitati et al.
5,588,745 A 12/1996 Tanaka et al.
5,624,184 A 4/1997 Chan
5,997,544 A 12/1999 Nies et al.
6,017,349 A * 1/2000 Heller ................ B01F 35/7162 366/139

(Continued)

FOREIGN PATENT DOCUMENTS

DE 3640279 A1 6/1987
DE 69812726 T2 2/2004

(Continued)

*Primary Examiner* — Nicholas W Woodall

(74) *Attorney, Agent, or Firm* — Dicke, Billig & Czaja, PLLC

(57) ABSTRACT

A device for providing a bone cement paste from two starting components, comprising a hollow cylindrical cartridge with an interior space, wherein, in a proximal part of the interior space, a bone cement powder is stored as the first starting component, and, in a distal part of the interior space, at least one bag containing a monomer liquid as the second starting component is stored, wherein the interior space is connectible at the proximal part of the interior space to a negative pressure source via a vacuum connector, wherein a dispensing plunger, which is movable axially in the interior space, is arranged between the bone cement powder and the at least one bag, and a feed plunger, which is movable axially in the interior space, is arranged on a side, axially opposite the dispensing plunger.

14 Claims, 9 Drawing Sheets

(56) References Cited

U.S. PATENT DOCUMENTS

| | | | | |
|---|---|---|---|---|
| 6,033,105 | A | 3/2000 | Barker et al. | |
| 6,544,233 | B1 * | 4/2003 | Fukui | A61M 5/31596 604/220 |
| 6,709,149 | B1 | 3/2004 | Tepic | |
| 7,073,936 | B1 * | 7/2006 | Jonsson | B01F 35/718 366/139 |
| 11,039,872 | B2 * | 6/2021 | Vogt | B01F 35/7174 |
| 2018/0132919 | A1 * | 5/2018 | Vogt | A61M 5/285 |
| 2018/0333176 | A1 * | 11/2018 | Vogt | A61B 17/8822 |
| 2019/0183552 | A1 * | 6/2019 | Kluge | A61B 17/8822 |

FOREIGN PATENT DOCUMENTS

| | | | |
|---|---|---|---|
| DE | 102009031178 | B3 | 9/2010 |
| EP | 0692229 | A1 | 1/1996 |
| EP | 0380867 | B1 | 8/1997 |
| EP | 0692229 | B1 | 12/1999 |
| EP | 1005901 | A2 | 6/2000 |
| EP | 1016452 | A2 | 7/2000 |
| EP | 1020167 | A2 | 7/2000 |
| EP | 0796653 | B1 | 5/2004 |
| EP | 1886647 | A1 | 2/2008 |
| EP | 3320869 | A1 | 5/2018 |
| WO | 9426403 | A1 | 11/1994 |
| WO | 9967015 | A1 | 12/1999 |

* cited by examiner

DEVICE AND METHOD FOR PROVIDING BONE CEMENT PASTE

CROSS-REFERENCE TO RELATED APPLICATIONS

This application claims priority pursuant to 35 U.S.C. 119(a) to European Application No. 22166434.5, filed Apr. 4, 2022, which application is incorporated herein by reference in its entirety.

Field of the Invention

The invention relates to a device for providing a bone cement paste from two starting components, comprising a hollow cylindrical cartridge with an interior space, wherein, in a proximal part of the interior space, a bone cement powder is stored as the first starting component, and, in a distal part of the interior space, at least one bag containing a monomer liquid as the second starting component is stored, wherein the interior space is connectible at the proximal part of the interior space to a negative pressure source via a vacuum connector, wherein a dispensing plunger, which is movable axially in the interior space, is arranged between the bone cement powder and the at least one bag, and a feed plunger, which is movable axially in the interior space (210), is arranged on a side, axially opposite the dispensing plunger, of the at least one bag, such that, when the dispensing plunger and the feed plunger are pushed together, the at least one bag is opened in a fluid-conducting manner, and the monomer liquid can flow into the distal part of the interior space, wherein the proximal part and the distal part of the interior space are fluidically connected to one another via a conduit.

The invention further relates to a method for providing a bone cement paste with such a device.

Background of the Invention

Considerable efforts are being made to demonstrate devices and methods for providing bone cement by means of which bone cement paste can be provided easily, reliably, and quickly. One important aspect of providing bone cement paste is the avoidance of air inclusions, e.g., gas bubbles, in the bone cement. To avoid this, a plurality of vacuum cementing systems have been described, of which the following are mentioned by way of example: U.S. Pat. Nos. 6,033,105 A, 5,624,184 A, 4,671,263 A, 4,973,168 A, 5,100,241 A, WO 99/67015 A1, EP 1020167 A2, U.S. Pat. No. 5,586,821 A, EP 1016452 A2, DE 3640279 A1, WO 94/26403 A1, EP 1005901 A2, EP 1886647 A1, and U.S. Pat. No. 5,344,232 A.

Within the market, there is a desire to simplify the provision of bone cement paste. One development consists of developing cementing systems in which both starting components are stored in separate regions of the mixing systems and are only mixed with one another in the cementing system immediately before the cementing application. Such closed, so-called full prepacked systems are mentioned in the following documents: EP 0 692 229 A1, DE 10 2009 031 178 B3, U.S. Pat. Nos. 5,997,544 A, 6,709,149 B1, DE 698 12 726 T2, EP 0 796 653 A2, and U.S. Pat. No. 5,588,745 A.

In the European patent EP 0 692 229 B1, a device is described in which a bag filled with monomer liquid is stored axially behind a region filled with a bone cement powder within a cartridge. A dispensing plunger is arranged between bone cement powder and bag. A feed plunger is arranged on the side, axially opposite the dispensing plunger, of the bag. In order to provide a bone cement paste, the dispensing plunger and feed plunger are pushed together, resulting in a fluid-conducting opening in the bag, and, as a result, the monomer liquid exits the bag. By continuing to push the two plungers together, the bag is compressed, and the monomer liquid is conveyed into the bone cement powder through a conduit in the dispensing plunger. The bone cement paste is provided by mixing the conveyed monomer liquid and the bone cement powder.

A disadvantage of such a device is that, to convey basically all of the monomer liquid into the bone cement powder, the bag must basically be compressed completely. Due to the stable and quite rigid wall of such commercial bags, this requires a considerable exertion of force by the user of the device, which increases the risk of injury when using the device. Furthermore, basically completely compressing such bags is impossible, and portion of the monomer liquid is therefore always left in the bag. In addition, when the bag is compressed, the formation of folds can occur in the bag wall which are filled with monomer liquid, sealed against the conduction of fluid, and prevent the essentially complete conveyance of the monomer liquid into the bone cement powder.

Objects

It is an object of the present invention to at least partially overcome one or more of the disadvantages resulting from the prior art.

In particular, the invention is based upon the goal of providing a device which allows essentially complete conveyance of monomer liquid from a bag into a bone cement powder and, at the same time, minimizes the force required of the user of the device as much as possible.

A further object of the invention is to provide a method with which bone cement can be provided from two starting components, by means of which at least some of the objects already described are achieved at least in part.

Preferred Embodiments of the Invention

The features of the independent claims contribute to at least partially achieving at least one of the aforementioned objects. The dependent claims provide preferred embodiments which contribute to at least partially achieving at least one of the objects.

A first embodiment of the invention is a device for providing a bone cement paste from two starting components, comprising: a hollow cylindrical cartridge with an interior space, wherein, in a proximal part of the interior space, a bone cement powder is stored as the first starting component, and, in a distal part of the interior space, at least one bag containing a monomer liquid as the second starting component is stored, wherein the interior space is connectible at the proximal part of the interior space to a negative pressure source via a vacuum connector, wherein a dispensing plunger, which is movable axially in the interior space, is arranged between the bone cement powder and the at least one bag, and a feed plunger, which is movable axially in the interior space, is arranged on a side, axially opposite the dispensing plunger, of the at least one bag, such that, when the dispensing plunger and the feed plunger are pushed together, the at least one bag is opened in a fluid-conducting manner, and the monomer liquid can flow into the distal part of the interior space, wherein the proximal part and the distal part of the interior space are fluidically connected to one another via a conduit, characterized in that the conduit extends from the dispensing plunger into the distal part of the interior space with an axial conduit length corresponding to at least a quarter of a bag length of the bag, so that, when pushed together, the dispensing plunger and the feed plunger are spaced apart by the conduit by a plunger spacing corresponding to one quarter of the bag length.

In one embodiment of the device, the conduit is substantially dimensionally stable. This embodiment is a second embodiment of the invention, which is preferably dependent upon the first embodiment of the invention.

In one embodiment of the device, the conduit is formed at least partially as a hollow cylinder with at least one fluid-conducting cylinder passage extending axially in a hollow cylinder wall. This embodiment is a third embodiment of the invention, which is preferably dependent upon the first or second embodiment of the invention.

In one embodiment of the device, the hollow cylinder has a hollow cylinder inner diameter which allows at least partial accommodation of the at least one bag. This embodiment is a fourth embodiment of the invention, which is preferably dependent upon the third embodiment of the invention.

In one embodiment of the device, the conduit is formed at least partially as a tube, as a hose, or as a tube and a hose. This embodiment is a fifth embodiment of the invention, which is preferably dependent upon the first or second embodiment of the invention, and in particular on the first or second embodiment of the invention.

In one embodiment of the device, the conduit has a conduit inner diameter of 0.5 mm to 2 mm. This embodiment is a sixth embodiment of the invention, which is preferably dependent upon one of the preceding embodiments of the invention.

In one embodiment of the device, at least one opening means for opening the at least one bag is arranged in the distal part of the interior space. This embodiment is a seventh embodiment of the invention, which is preferably dependent upon one of the preceding embodiments of the invention.

In one embodiment of the device, the opening means is formed as a mandrel, the opening means has at least one cutting edge, or is formed as a mandrel, and has at least one cutting edge. This embodiment is an eighth embodiment of the invention, which is preferably dependent upon the seventh embodiment of the invention.

In one embodiment of the device, a proximal interior space end, axially opposite the dispensing plunger, of the proximal part of the interior space is sealed against the conduction of fluid by a cartridge head. This embodiment is a ninth embodiment of the invention, which is preferably dependent upon one of the preceding embodiments of the invention.

In one embodiment of the device, the vacuum connector is arranged on the cartridge head. This embodiment is a tenth embodiment of the invention, which is preferably dependent upon the ninth embodiment of the invention.

In one embodiment of the device, a mixing tube that is axially displaceable in the proximal part of the interior space is arranged in a cartridge head passage of the cartridge head. This embodiment is an eleventh embodiment of the invention, which is preferably dependent upon the ninth or tenth embodiment of the invention.

In one embodiment of the device, a releasable mixing rod is arranged within the mixing tube. This embodiment is a twelfth embodiment of the invention, which is preferably dependent upon the eleventh embodiment of the invention.

A thirteenth embodiment of the invention is a method for providing a bone cement paste from two starting components by means of a device according to one of the preceding embodiments of the invention, comprising the following steps:

a. pushing the dispensing plunger and feed plunger together while opening the at least one bag;
b. continuing to push together the feed plunger and dispensing plunger until the conduit is arranged on the feed plunger;
c. conveying the monomer liquid through the conduit into the proximal part of the interior space by applying a negative pressure at the vacuum connector.

In one embodiment of the method using a device according to the twelfth embodiment of the invention, the bone cement powder and the monomer liquid are mixed in the proximal part of the interior space in a step d. by means of the mixing rod with applied negative pressure while providing the bone cement paste. This embodiment is a fourteenth embodiment of the invention, which is preferably dependent upon the thirteenth embodiment of the invention.

In one embodiment of the method, in a step e., the mixing rod is detached from the mixing tube, the mixing rod is pulled out of the mixing tube, and the mixed bone cement paste is discharged from the proximal part of the interior space through the mixing tube out of the device by advancing the dispensing plunger in the direction of the cartridge head. This embodiment of the invention is a fifteenth embodiment of the invention, which is preferably dependent upon the fourteenth embodiment of the invention.

General

In the present description, range specifications also include the values specified as limits. An indication of the type "in the range of X to Y" with respect to a variable A consequently means that A can assume the values X, Y and values between X and Y. Ranges delimited on one side of the type "up to Y" for a variable A accordingly mean, as a value, Y and less than Y.

Some of the described features are linked to the term, "substantially." The term, "substantially," is to be understood as meaning that, under real conditions and manufacturing techniques, a mathematically exact interpretation of terms such as "superimposition," "perpendicular," "diameter," or "parallelism" can never be given exactly, but only within certain manufacturing-related error tolerances. For example, "substantially parallel axes" include an angle of 85 degrees to 95 degrees to one another, and "substantially equal volumes" include a deviation of up to 5 vol %. A "device consisting substantially of plastic material" comprises, for example, a plastic content of ≥95 to ≤100 wt %. "Essentially adding all of a volume B" comprises, for example, adding ≥95 to ≤100 vol % of the total volume of B. "Essentially conveying all of a component C" comprises, for example, conveying ≥90 to ≤100 vol %, and in particular ≥95 to ≤100 vol %, of the total volume of C.

The terms, "proximal" and "distal," are used only to designate the spatially opposite ends of the device or other structural units of the device, and do not permit any inference as to orientation with respect to a human body, such as a user of the device. "Distally to . . . " and "proximally to . . . " or similar formulations correspondingly express only the spatial arrangement of two structural units of the device in relation to one another.

DETAILED DESCRIPTION

An initial subject of the invention relates to a device for providing a bone cement paste from two starting components, comprising: a hollow cylindrical cartridge with an interior space, wherein, in a proximal part of the interior space, a bone cement powder is stored as the first starting component, and, in a distal part of the interior space, at least one bag containing a monomer liquid as the second starting component is stored, wherein the interior space is connectible at the proximal part of the interior space to a negative pressure source via a vacuum connector, wherein a dispensing plunger, which is movable axially in the interior space, is arranged between the bone cement powder and the at least one bag, and a feed plunger, which is movable axially in the interior space, is arranged on a side, axially opposite the dispensing plunger, of the at least one bag, such that, when the dispensing plunger and the feed plunger are pushed together, the at least one bag is opened in a fluid-conducting manner, and the monomer liquid can flow into the distal part of the interior space, wherein the proximal part and the distal part of the interior space are fluidically connected to one another via a conduit, characterized in that the conduit extends from the dispensing plunger into the distal part of the interior space with an axial conduit length corresponding to at least a quarter of a bag length of the bag, so that, when pushed together, the dispensing plunger and the feed plunger are spaced apart by the conduit by a plunger spacing corresponding to one quarter of the bag length.

The device has a conduit through which the distal part and the proximal part of the interior space are connected to one another in a fluid-conducting manner. Fluid-conducting means that the distal part and the proximal part of the interior space are connected in a manner permeable to liquids—in particular, the monomer liquid—and to gases.

The conduit extends within the distal part of the interior space, starting from the dispensing plunger in the direction of the feed plunger, wherein, within the distal part of the interior space, it has an axial conduit length which corresponds to at least one quarter of a bag length of the bag. Preferably, the conduit and the at least one bag are arranged at least partially next to one another in the distal part of the interior space, so that the device is formed to be as compact as possible. The conduit also extends through the dispensing plunger or past the dispensing plunger in order to connect the distal part of the interior space to the proximal part of the interior space in a fluid-conducting manner. In this case, the section of the conduit extending into the distal part of the interior space and the section of the conduit extending through the dispensing plunger or past the dispensing plunger can be configured in one piece or in multiple parts.

Since the at least one bag is preferably mounted with its longitudinal axis parallel to the longitudinal axis of the device for steric reasons, and the distance between the dispensing plunger and the feed plunger when the device is in the resting state preferably corresponds substantially to the bag length, the axial conduit length in the resting state preferably corresponds substantially to at least one quarter of the distance from the dispensing plunger to feed plunger.

When the dispensing plunger and the feed plunger are pushed together, wherein the dispensing plunger is preferably displaced in the direction of the feed plunger and the feed plunger preferably remains substantially at its original location, the at least one bag is opened in a fluid-conducting manner, e.g., by exerting pressure on the bag, and the monomer liquid exits into the distal part of the interior space. In this case, the dispensing plunger and the feed plunger can be moved towards each other until the conduit is arranged with a conduit end, which faces the feed plunger, on the feed plunger, and preferably touching the feed plunger, and continued pushing together is impossible without destroying the structural integrity of the conduit. The conduit therefore separates the dispensing plunger and the feed plunger with a plunger spacing which corresponds to at least one quarter of the bag length.

After the dispensing plunger and feed plunger have been pushed together, the conduit therefore ensures a plunger spacing which corresponds to at least one quarter of the bag length, and at the same time allows basically all the monomer liquid adjoining the feed plunger to be conveyed into the proximal part of the interior space by leaving the bag. The conduit is therefore configured in such a way that conveying basically all of the monomer liquid from the at least one bag into the proximal part of the interior space is possible without the at least one bag having to be basically completely compressed, and the dispensing plunger and the feed plunger having to be pushed together basically completely, and spaced apart only by the compressed bag. This makes it easier for the user of the device to use the device, since basically completely pressing together the at least one bag requires considerable exertion of force on the part of the user. In addition, there is a risk of cavities filled with monomer liquid forming in the bag while basically completely compressing the at least one bag, so that the monomer liquid cannot flow basically completely out of the bag, and conveying basically all the monomer liquid into the proximal part of the interior space is prevented.

It is advantageous to collect the monomer liquid after it flows out of the fluid-conducting, opened bag adjoining the feed plunger, and to convey it from there into the proximal part of the interior space instead of collecting the monomer liquid adjacent to the dispensing plunger and conveying it from there, e.g., through a fluid-conducting passage through the dispensing plunger, into the proximal part of the interior space. The latter entails a risk of uncontrolled and/or undesired flow of the monomer liquid into the proximal part of the interior space, which would result in uncontrolled and/or undesired formation of a bone cement paste. It is preferred that the device have, in addition to the conduit, no further means, such as, for example, additional passages through the dispensing plunger, which connect the distal part to the proximal part of the interior space in a fluid-conducting manner.

In order to ensure reliable, fluid-conducting opening of the at least one bag by pushing together the dispensing plunger and feed plunger, the axial conduit length and/or the plunger spacing preferably corresponds to a maximum of three-quarters of the bag length.

In one embodiment, the dispensing plunger and the conduit are designed as one piece.

The monomer liquid is preferably conveyed through the conduit by applying negative pressure in the proximal part of the interior space via the vacuum connector by means of a negative pressure source, e.g., a vacuum pump, whereby the monomer liquid is sucked out of the distal part of the interior space through the conduit.

In order to prevent bone cement powder from being able to pass from the proximal part into the distal part of the interior space and the at least two bags—in particular, bag part pieces—from the distal part to the proximal part of the interior space via the conduit, the conduit is preferably equipped with filter means—in particular, a porous disk—for example, made of sintered polypropylene particles, of sintered or compressed polyethylene fibers, of cellulose felt, or of cardboard, which makes the conduit impermeable to solids.

Within the distal part of the interior space of the device, at least one, preferably one to three, and more preferably one to two, bags containing a monomer liquid are stored. A bag is understood to mean a non-rigid, largely flexible storage option which can store the monomer liquid in a hermetically sealed and sterile manner and can be opened by the exertion of pressure or action of an opening means—for example, by piercing, cutting open, or tearing open. The bags can be manufactured, for example, from a multilayer composite film—preferably comprising an EVOH barrier layer. Optionally, the bags can have a metal coating, and in particular an aluminum coating.

The device has a hollow cylindrical cartridge. A hollow cylindrical cartridge is to be understood as a tubular receptacle which has an interior space and a cartridge wall surrounding the interior space. The cross-section of the cartridge can assume any shape. Because the device is easy to manufacture and safe to use, the cross-section, and preferably also the cross-section of the interior space, is of circular design. This allows easy handling for the user and reduces a risk of movable parts wedging within the device, due to the absence of edges. According to the invention, the cartridge can consist of a wide variety of materials or material combinations. For example, the device can consist of a polymer. The polymer is preferably a transparent polymer, since this allows the user to visually check proper functioning of the device during use.

A dispensing plunger which is movable axially in the interior space is arranged between the bone cement powder and the bag. The dispensing plunger serves to spatially separate the at least one bag and the bone cement powder so that neither the bone cement powder can pass from the proximal part of the interior space into the distal part of the interior space, nor can the at least one bag pass from the distal part of the interior space into the proximal part of the interior space. In particular, the latter prevents a bone cement paste from containing a bag or bag pieces, which can represent health risks for the patient and could impair proper dispensing of the bone cement paste from the device. The dispensing plunger divides the interior space into the proximal and distal parts of the interior space. The dispensing plunger preferably also serves to dispense the provided bone cement paste from the device. For this purpose, the dispensing plunger can be axially displaced from its original position in the direction of the provided bone cement paste.

The device has a feed plunger which is axially movable in the interior space. The feed plunger is arranged inside the device on the side, axially opposite the dispensing plunger, of the at least one bag. By means of a relative movement of the feed plunger and dispensing plunger relative to each other, which shortens the distance between the feed plunger and dispensing plunger within the interior space, e.g., by moving the feed plunger in the direction of the dispensing plunger, or preferably by moving the dispensing plunger in the direction of the feed plunger, the at least one bag is opened—for example, due to the bag bursting from the exertion of pressure by the two plungers.

In order to prevent the dispensing plunger and feed plunger from being pushed together unintentionally, a latching means can be arranged on the dispensing plunger and/or on the feed plunger so that the dispensing plunger and/or the feed plunger can latch with the cartridge, and in particular with the cartridge wall. To open the at least one bag, the dispensing plunger is preferably displaced in the direction of the feed plunger, since this allows more space in the proximal part of the interior space to thoroughly mix the bone cement paste consisting of the starting components. It is therefore preferred that in particular the feed plunger not be unintentionally displaceable out of its original position, and in particular by forces which act on the feed plunger while the at least one bag is opened.

In this case, the latching means ensures that the at least one bag can first be opened by advancing the dispensing plunger, and the monomer liquid exiting therefrom can be pressed and/or sucked through the conduit into the proximal part of the interior space of the cartridge, i.e., into the bone cement powder, wherein the feed plunger holds its original position relative to the cartridge and to the interior space. Only after the monomer liquid has been largely pressed and/or sucked into the bone cement powder, and the bone cement paste is therefore present in the proximal part of the interior space of the cartridge, can the bone cement paste subsequently be pressed out of the proximal part of the cartridge with the feed plunger. The force for releasing the latching is therefore greater than the force necessary for opening the at least one bag and conveying the monomer liquid through the conduit into the proximal part of the interior space.

In one embodiment, the conduit can be shortened in its axial conduit length by pushing the dispensing plunger and the feed plunger together, e.g., by compressing the conduit, or bending or kinking it radially to the longitudinal axis of the device. In this embodiment, the plunger spacing caused by the conduit can be shorter than the axial conduit length. Preferably, the conduit is configured such that the plunger spacing caused by the conduit corresponds to at least 90% of the axial conduit length.

In a preferred embodiment, the conduit is substantially dimensionally stable, so that the plunger spacing caused by the conduit corresponds to the axial conduit length. The axial conduit length is substantially not changed by pushing together the dispensing plunger and the feed plunger.

The conduit can be shaped differently in order to space apart the dispensing plunger and the feed plunger with the plunger spacing and, at the same time, ensure that the monomer liquid is conveyed into the proximal part of the interior space.

One embodiment of the device is characterized in that the conduit is formed at least partially as a hollow cylinder, and preferably as a continuous hollow cylinder, with at least one fluid-conducting cylinder passage extending axially in a hollow cylinder wall. In this case, the hollow cylinder wall provides the spacing of the feed plunger and the dispensing plunger with the plunger spacing, and the cylinder passage within the hollow cylinder wall, which preferably opens in a hollow cylinder end facing the feed plunger, allows the monomer liquid to be conveyed into the proximal part of the interior space. In order to ensure that the monomer liquid is conveyed as independently as possible from the spatial orientation of the device, it is preferred that the hollow cylinder have at least three, preferably at least four, and more preferably at least six, cylinder passages. The hollow cylinder preferably has a maximum of ten cylinder passages. Preferably the cylinder passages are distributed uniformly over the hollow cylinder.

In one embodiment, the hollow cylinder is formed from separate hollow cylindrical segments, and in particular separate hollow cylindrical segments extending in the axial direction, wherein it is preferred that at least one cylinder passage be formed in each of the hollow cylinder segments. For example, the hollow cylinder can be subdivided into two to eight, and preferably four to six, hollow cylindrical segments.

In order to configure the device to be as compact and as resilient as possible, one embodiment of the device is characterized in that the hollow cylinder has a hollow cylinder inner diameter, which allows at least partial accommodation of the at least one bag. Preferably, the inner hollow cylinder diameter corresponds to at least one bag width of the bag, so that the at least one bag and, when several bags are present, all bags, can be mounted, or can be mounted at least partially, with the radial circumference within the hollow cylinder. As a result, the bag or bags can be mounted so as to be "pushed" into the hollow cylinder. This allows a space-saving arrangement of the at least one bag within the distal part of the interior space. Preferably, the hollow cylinder wall extends substantially directly adjacently to the cartridge wall, which allows a compact configuration of the device.

One embodiment of the device is characterized in that the conduit is formed at least partially as a tube, as a hose, or as a tube and as a hose. This allows simple production and easy and space-saving arrangement of the conduit within the distal part of the interior space. In this case, the shape as a tube is preferred, since a tube is dimensionally stable and therefore allows the dispensing plunger and feed plunger to the spaced apart by the conduit. The conduit can be formed from one or more tubes and/or hoses. Preferably, the conduit comprises one to six, and preferably one to four, tubes and/or hoses.

In order to facilitate the fastest possible conveyance of the monomer liquid through the conduit into the proximal part of the interior space, one embodiment of the device is characterized in that the conduit has a fluid-conducting internal diameter in a range of 0.5 mm to 2 mm, and preferably in a range of 0.5 mm to 1.5 mm. Smaller diameters slow down the conveyance of the monomer liquid. Larger diameters make it more difficult to convey basically all of the monomer liquid, due to lower capillary effects in the conduit.

The at least one bag can, for example, be opened in a fluid-conducting manner, when the dispensing plunger and the feed plunger are pushed together, by exerting pressure which is exerted by the two plungers on the bag.

In order to facilitate fluid-conducting opening of the bag by pushing the dispensing plunger and feed plunger together, one embodiment of the device is characterized in that at least one opening means for opening the bag is arranged in the distal part of the interior space.

An opening means is understood to mean a molded structural unit or structural subunit which opens, and in particular pierces, cuts, or tears open, a bag when the opening means and the bag are pushed against each other. In order to facilitate opening—in particular, plugging, cutting, or tearing open—it is preferred that the opening means be able to be pressed against the bags with a small surface area compared to a cross-sectional area of the interior space, i.e., the opening means are "sharp" and/or "pointed" in the broadest sense.

Depending upon the nature of the bag and the opening means, a different application of high force can be necessary for opening the bag by the opening means. In particular, the application of force by the opening means is reduced, compared to a required application of force by opening the at least one bag by means of two planar plungers.

In one embodiment, at least one opening means is arranged on the dispensing plunger. In a further embodiment, at least one opening means is arranged on the feed plunger. In a further preferred embodiment, at least one opening means is arranged on the dispensing plunger, and at least one opening means is arranged on the feed plunger, which facilitates fluid-conducting opening of the at least one bag even when the dispensing plunger and the feed plunger are pushed together slightly.

In one embodiment, the conduit is formed as an opening means. For example, the conduit can be formed as a tube, wherein the conduit is tapered at the end facing the feed plunger—for example, as a mandrel. The conduit therefore facilitates the fluid-conducting opening of the at least one bag.

One embodiment of the device is characterized in that the opening means is formed as a mandrel. Another embodiment is characterized in that the opening means has at least one cutting edge. Another embodiment of the device is characterized in that the opening means is formed as a mandrel and has at least one cutting edge.

In order to prevent unintentional opening of the at least one bag, e.g., while transporting the device, it can be preferred that a transport lock be arranged in the distal part of the interior space between the opening means and the at least one bag. The transport lock can be formed, for example, from a plate with perforations for the subsequent passage of the opening means, which are spaced apart on the distal side of the dispensing plunger by means of webs which bend when the force is applied.

One embodiment of the device is characterized in that a proximal interior space end, axially opposite the dispensing plunger, of the proximal portion of the interior space is fluidic ally closed by a cartridge head. The cartridge head is preferably reversibly connectible to the cartridge, e.g., by means of a threaded connection, and allows the proximal portion of the interior space to be easily filled with the bone cement powder. In one embodiment, the cartridge and the cartridge head are designed as one piece.

One embodiment of the device is characterized in that the vacuum connector is arranged on the cartridge head. This makes it easy to produce the device and, at the same time, places the vacuum connector spatially as far away as possible from the dispensing plunger and in particular from the conduit, so that the monomer liquid conveyed by the conduit into the proximal part of the interior space is not unintentionally conveyed directly via the vacuum connector into the negative pressure source connectible to the device.

The bone cement paste provided in the device can be discharged from the device in different ways.

One embodiment of the device is characterized in that a fluid-conducting cartridge head passage is arranged in the cartridge head through which the bone cement paste provided in the device—in particular, in the proximal part of the interior space by means of the bone cement powder and the monomer liquid—can be discharged. For this purpose, the dispensing plunger can preferably be displaced in the direction of the cartridge head, which causes the bone cement paste to be pressed out of the device. Preferably, the dispensing plunger is moved in the direction of the cartridge head by advancing the feed plunger. The feed plunger exerts a force on the conduit which transfers it to the dispensing plunger.

In order to mix the two starting components while providing the bone cement paste, one embodiment of the device is characterized in that a fluid-conducting mixing tube that is displaceable axially in the proximal part of the interior space is arranged in the cartridge head passage. In one embodiment, a mixing element, e.g., in the form of a stirrer, can be introduced through the mixing tube from outside the device into the proximal part of the interior space in order to mix the starting components after the monomer liquid has been conveyed through the conduit into the proximal part of the interior. For example, a mixing element can be inserted into the mixing tube far enough for the mixing element to protrude from the mixing tube into the proximal part of the interior space, and the starting components are mixed by the mixing element by repeated, axial, upward and downward movement of the mixing tube. In a preferred embodiment, the mixing tube itself has a mixing element, in order to mix the starting components by repeated, axial, upward and downward movement of the mixing tube. A mixing disk is preferably arranged on a mixing tube end facing the dispensing plunger.

After the starting components have been mixed, and if necessary after removal of the mixing rod from the mixing tube, the mixing tube can be used as a dispensing snorkel for the controlled delivery of the bone cement paste from the device. For this purpose, the mixing tube is preferably pulled axially out of the cartridge head as far as possible and then fixed to the cartridge head—for example, by means of a screw thread.

One embodiment of the device is characterized in that a detachable mixing rod for improved mixing of the starting components within the proximal part of the interior space is arranged within the mixing tube. The mixing rod can represent a mixing element which extends axially through the mixing tube and is fixedly connected to the mixing tube for mixing the starting components. For this purpose, the mixing rod preferably has a mixing element on a mixing rod end facing the dispensing plunger.

If the mixing tube already has a mixing element, the mixing rod makes it easier to operate the mixing tube. In addition, the mixing rod improves the handling of the device and reduces the risk of the mixing tube kinking when the starting components are mixed. Furthermore, the mixing rod fluidically closes the mixing tube and thereby prevents the starting components from accumulating within the mixing tube, which are inaccessible to thorough mixing through the mixing tube within the mixing rod.

At a mixing rod end opposite the discharge plunger, the mixing rod preferably has a handle for reversibly moving the mixing rod together with the mixing tube connected thereto up and down axially in the proximal part of the interior space in order to mix the starting components.

The mixing rod is preferably detachably connected to the mixing tube via the handle, so that the mixing rod can be pulled out of the mixing tube by removing the handle. As a result, after the bone cement paste has been provided, the mixing tube can be used as a dispensing snorkel for the bone cement paste. For this purpose, the mixing tube is preferably pulled out of the device as far as possible and subsequently firmly connected to the cartridge head so that the mixing tube is no longer axially movable. This can preferably take place via a screw thread.

Another subject of the invention relates to methods for providing a bone cement paste from two starting components by means of an embodiment of the above-describe device, comprising the following steps:

a. pushing the dispensing plunger and feed plunger together while opening the at least one bag;
b. continuing to push together the feed plunger and dispensing plunger until the conduit is arranged on the feed plunger;
c. conveying the monomer liquid through the conduit into the proximal part of the interior space by applying a negative pressure at the vacuum connector.

By pushing the dispensing plunger and feed plunger together, a fluid-conducting opening of the at least one bag arises, so that the monomer liquid contained in the bag flows out into the distal part of the interior space. Preferably, the dispensing plunger and feed plunger are pushed together such that the dispensing plunger is displaced in the direction of the feed plunger, while the feed plunger remains substantially at its original position within the cartridge. This provides a spatial enlargement of the proximal part of the interior space so that subsequent mixing of the bone cement paste from the two starting components is facilitated. In order to be able to open the at least one bag more easily by pushing together the two plungers, it is preferable for opening to be assisted by means of an opening means, such as, for example, a mandrel on at least one of the two plungers.

After the at least one bag is opened, the dispensing plunger and the feed plunger are pushed together until the conduit is arranged on the feed plunger—in particular, until the conduit is in contact with the feed plunger—and the two plungers are therefore spaced apart by the conduit. The conduit ensures that the monomer liquid can be conveyed from the region of the distal part of the interior space that is spatially adjacent to the feed plunger into the proximal part of the interior space. In this case, due to the design of the conduit, the at least one bag does not have to be compressed basically completely, which facilitates the use of the device for the user due to a smaller amount of force and also reduces the risk of monomer liquid inclusions within an otherwise compressed bag.

A portion of the monomer liquid leaving the at least one bag can already be conveyed into the proximal part of the interior space by continuing to push together the feed plunger and dispensing plunger after the bag has been opened. In order to allow basically all of the monomer liquid to be conveyed out of the distal part into the proximal part of the interior space, a negative pressure is applied to the vacuum connector—preferably only after the conduit is arranged on the feed plunger—e.g., by connecting the vacuum connector to a vacuum pump.

One embodiment of the method is characterized in that, after the substantially complete conveying of the monomer liquid into the proximal part of the interior space, the bone cement powder and the monomer liquid in the proximal part of the interior space are mixed by means of a mixing rod with applied negative pressure while providing the bone cement paste. Preferably, the mixing rod is actuated from outside the device. Mixing while applying negative pressure reduces gas inclusions in the provided bone cement paste, which contributes to improved mechanical strength of the bone cement produced by curing from the bone cement paste.

The provided bone cement paste can be discharged from the device in different ways. For example, the bone cement paste can be removed from the proximal interior space with a spatula.

One embodiment of the method is characterized in that, after the bone cement paste has been mixed, the mixing rod used for this purpose is detached from the mixing tube of the device and removed therefrom by pulling, so that the mixed bone cement paste is discharged from the device from the proximal part of the interior space through the mixing tube by advancing the dispensing plunger in the direction of the cartridge head. Preferably, the dispensing plunger is predriven by advancing the feed plunger, which acts, via the conduit, on the dispensing plunger. This reduces the work steps of the user necessary for discharging the bone cement paste, and the tools necessary for this purpose.

In order to dispense the bone cement paste from the device, the device is preferably connected to a dispensing aid—in particular, a dispensing gun—which displaces the feed plunger, and therefore also the dispensing plunger, in the direction of the cartridge head and therefore expels the bone cement paste from the proximal part of the interior space.

The device is characterized in that it provides a bone cement paste from two starting components. Bone cement paste is understood to mean a substance that is suitable in the field of medical technology for creating a stable connection between artificial joints, such as hip and knee joints, and bone material. By curing, a bone cement paste becomes a bone cement. These bone cements are preferably polymethyl methacrylate bone cements (PMMA bone cements). PMMA bone cements have been used for a long time in medical applications and are based upon the work of Sir Charnley (cf. Charnley, J., Anchorage of the femoral head prosthesis of the shaft of the femur. *J. Bone Joint Surg.* 1960; 42, 28-30). In this case, PMMA bone cements can be produced from a cement powder as the first starting component and a monomer liquid as the second starting component. With a suitable composition, the two starting components can be storage-stable, separately from one another. When the two starting components are brought into contact with one another, a plastically-deformable bone cement paste is produced by the swelling of the polymer components of the bone cement powder. In this case, polymerization of the monomer by radicals is initiated. As the polymerization of the monomer progresses, the viscosity of the bone cement paste increases until it cures completely.

Bone cement powder is understood to mean a powder that comprises at least one particulate polymethyl methacrylate and/or a particulate polymethyl methacrylate copolymer. Examples of copolymers are styrene and/or methyl acrylate. In one embodiment, the bone cement powder can additionally comprise a hydrophilic additive, which supports the distribution of the monomer liquid within the bone cement powder. In a further embodiment, the bone cement powder can additionally comprise an initiator, which initiates the polymerization. In a further embodiment, the bone cement powder can additionally comprise a radiopaque material. In yet another embodiment, the bone cement powder can additionally comprise pharmaceutically-active substances, such as antibiotics.

The bone cement powder preferably comprises, as a hydrophilic additive, at least one particulate polymethyl methacrylate and/or a particulate polymethyl methacrylate copolymer, an initiator, and a radiopaque material, or consists of these components. More preferably, the bone cement powder comprises at least one particulate polymethyl methacrylate and/or a particulate polymethyl methacrylate copolymer, an initiator, a radiopaque material, and a hydrophilic additive, or consists of these components. Most preferably, the bone cement powder comprises at least one particulate polymethyl methacrylate and/or a particulate polymethyl methacrylate copolymer, an initiator, a radiopaque material, a hydrophilic additive, and an antibiotic, or consists of these components.

According to the invention, the particle size of the particulate polymethyl methacrylate and/or of the particulate polymethyl methacrylate copolymer of the bone cement powder can correspond to the sieve fraction of less than 150 μm, and preferably less than 100 μm.

According to the invention, the hydrophilic additive can be designed in particulate and/or fibrous form. In a further embodiment, the hydrophilic additive can be slightly soluble, and preferably insoluble, in methyl methacrylate. In a further embodiment, the hydrophilic additive can have an absorption capacity of at least 0.6 g methyl methacrylate per gram of hydrophilic additive. In a further embodiment, the hydrophilic additive can comprise a chemical substance comprising at least one OH group. In this case, the hydrophilic additive can preferably have covalently-bonded OH groups at its surface. Examples of such preferred hydrophilic additives can be additives selected from the group comprising cellulose, oxycellulose, starch, titanium dioxide, and silicon dioxide, wherein pyrogenic silicon dioxide is particularly preferred. In one embodiment, the particle size of the hydrophilic additive can correspond to the sieve fraction of less than 100 μm, preferably less than 50 μm, and most preferably less than 10 μm. The hydrophilic additive can be contained in an amount of 0.1 to 2.5 wt %, relative to the total weight of the bone cement powder.

According to the invention, the initiator can contain dibenzoyl peroxide or consist of dibenzoyl peroxide.

According to the invention, a radiopaque material is understood to mean a substance that makes it possible to make the bone cement visible on diagnostic X-ray images. Examples of radiopaque materials can include barium sulfate, zirconium dioxide, and calcium carbonate.

According to the invention, the pharmaceutically-active substance can comprise one or more antibiotics and, optionally, added cofactors for the one or more antibiotics. Preferably, the pharmaceutically-active substance consists of one or more antibiotics and, optionally, added cofactors for the one or more antibiotics. Examples of antibiotics include, inter alia, gentamicin, clindamycin, and vancomycin.

According to the invention, the monomer liquid can comprise the monomer methyl methacrylate or consist of methyl methacrylate. In one embodiment, the monomer liquid comprises, in addition to the monomer, an activator dissolved therein, such as N,N-dimethyl-p-toluidine, or consists of methyl methacrylate and N,N-dimethyl-p-toluidine.

The features disclosed for the device are also disclosed for the method, and vice versa.

FIGURES

In the following, the invention is illustrated further, by way of example, by figures. The invention is not limited to the figures. Shown are:

FIG. 1 a schematic longitudinal section of a device for providing a bone cement paste, comprising two bags containing a monomer liquid and a conduit in the form of a hollow cylinder, FIG. 2 the device from FIG. 1, with fluid-conducting open bags, FIG. 3 the device from FIGS. 1 and 2, wherein a dispensing plunger and a feed plunger of the device are spaced apart by the conduit, FIG. 4 the device from FIGS. 1 through 3, wherein basically all of the monomer liquid has been conveyed through the conduit, FIG. 5 the device from FIGS. 1 through 4, with provided bone cement paste, FIG. 6 the device from FIGS. 1 through 5, ready for dispensing the bone cement paste, FIG. 7 the device from FIGS. 1 through 6, when discharging the provided bone cement paste, FIG. 8 a schematic longitudinal section through a further device for providing a bone cement paste, comprising a conduit in the form of four tubes, and FIG. 9 a flowchart of a method for providing a bone cement paste.

Figure 1:
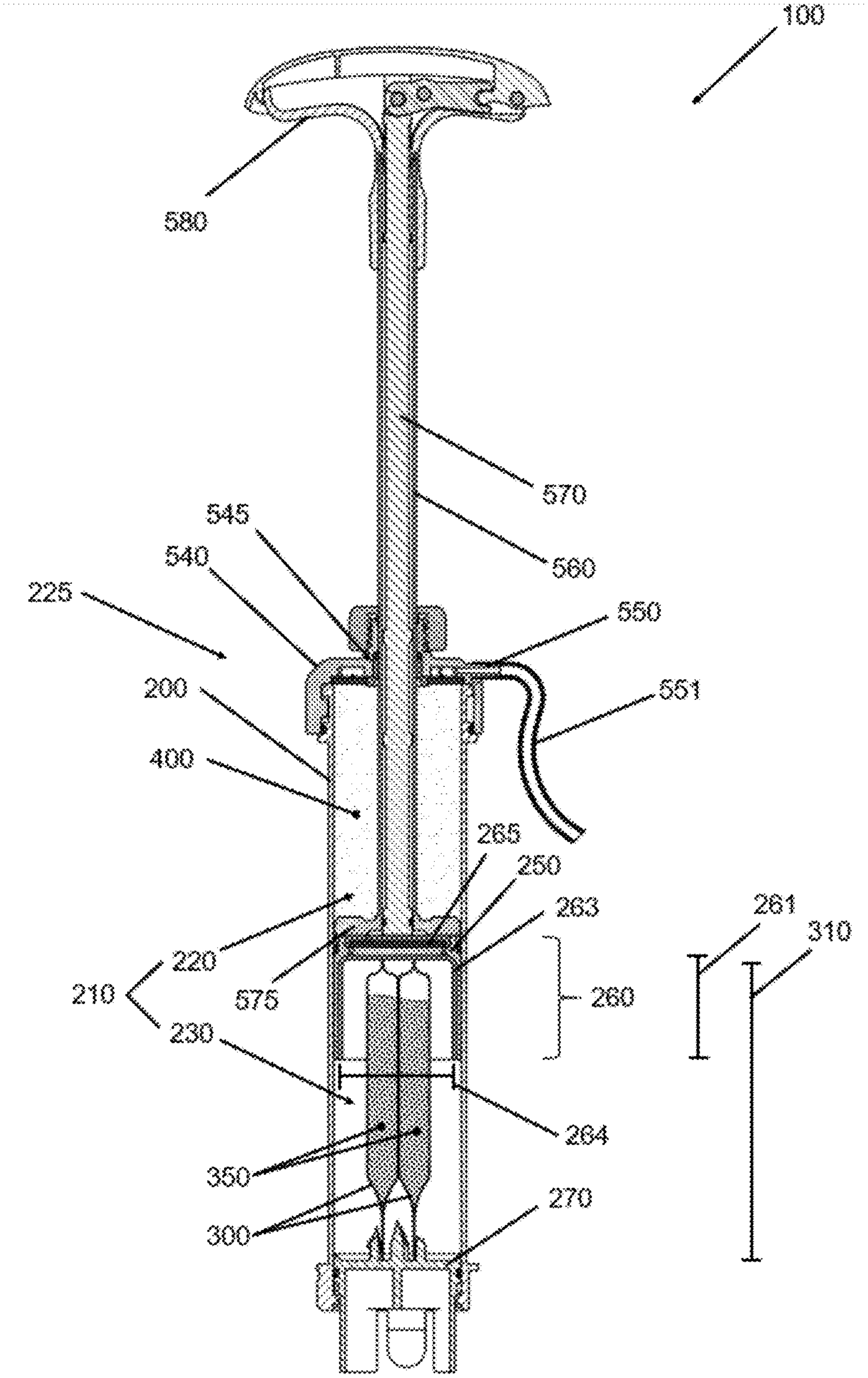
FIG. 1 shows a schematic longitudinal section of a further exemplary embodiment of a device 100 for providing a bone cement paste in a starting state. The device 100 is constructed in one piece, but from several components. The device 100 is constructed in a tubular manner and comprises a hollow cylindrical cartridge 200 with an interior space 210. Bone cement powder 400 is stored in a proximal part 220 of the interior space 210 as a first starting component, and two bags 300 containing a monomer liquid 350 are stored in a distal part 230 of the interior space 210 as the second starting component of the bone cement paste.

The proximal part 220 and the distal part 230 of the interior space 210 are separated by a dispensing plunger 250 which is reversibly movable in the interior space 210. The dispensing plunger 250 is designed to be impermeable to solids so that no bone cement powder 400 passes from the proximal part 210 into the distal part 230 of the interior space 210, and the bags 300 do not pass from the distal part 230 to the proximal part 220 of the interior space 210. For this purpose, the dispensing plunger 250 has a porous disk 265.

The dispensing plunger 250 has a conduit 260 which fluidically connects the distal part 230 to the proximal part 220 of the interior space. The conduit 260 extends in a tunnel-like manner through the dispensing plunger and is formed in sections as a hollow cylinder, with fluid-conducting cylinder passages 263 (provided with reference points only by way of example), which extends distally from the dispensing plunger 250 in the direction of a feed plunger 270 which is arranged on the axially opposite side of the bags 300 in the interior space 210. The conduit 260 has an axial conduit length 261 which corresponds approximately to one-third of an axial bag length 310 of the bags 300. The conduit 300 in the form of a hollow cylinder has a hollow cylinder inner diameter 264, which allows the bags 300 to be axially inserted partially into the cavity surrounding the hollow cylinder. This allows the design of the device 100 to be as compact as possible. In the shown embodiment, the conduit 260 and the dispensing plunger 250 are designed as one piece.

The feed plunger 270 fluidically closes a distal interior space end so that the monomer liquid 350 cannot inadvertently escape there. The feed plunger 270 is reversibly displaceable axially in the interior space 210 and is designed to be reversibly connectible to a discharge gun (not shown) in order to make it easier for the user to actually displace it in the interior space 210.

At a proximal interior space end 225 of the proximal part 220 of the interior space 210, the cartridge 200 is closed with a cartridge head 540 so that the bone cement powder 400 cannot inadvertently escape from the interior space 210. The cartridge head 540 has a cartridge head passage 545 in the middle, through which a mixing tube 560 is inserted in an axially-movable manner into the proximal part 220 of the interior space 210. A mixing rod 570 is arranged within the mixing tube 560 and is detachably fastened to the mixing tube 560 by a handle 580 on a proximal mixing tube end and is therefore axially movable together with the mixing tube 560 in the proximal part 220 of the interior space 210. The handle 580 makes it easier for the user to handle the device 100 by facilitating an axial movement of the mixing tube 560 together with the mixing rod 570 within the interior space 210. At a distal mixing tube end facing the dispensing plunger 250, the mixing tube 560 is equipped with a mixing disk 575, which facilitates mixing of monomer liquid 350 and bone cement powder 400.

A vacuum connector 550, via which the proximal part 220 of the interior space 210 can be fluidically connected to a negative pressure source (not shown), is attached to the cartridge head 540. In the shown embodiment, the vacuum connector 550 is shaped as a tubular protrusion, which makes the interior space 210 connectible to the negative pressure source by means of a hose 551.

Figure 2:
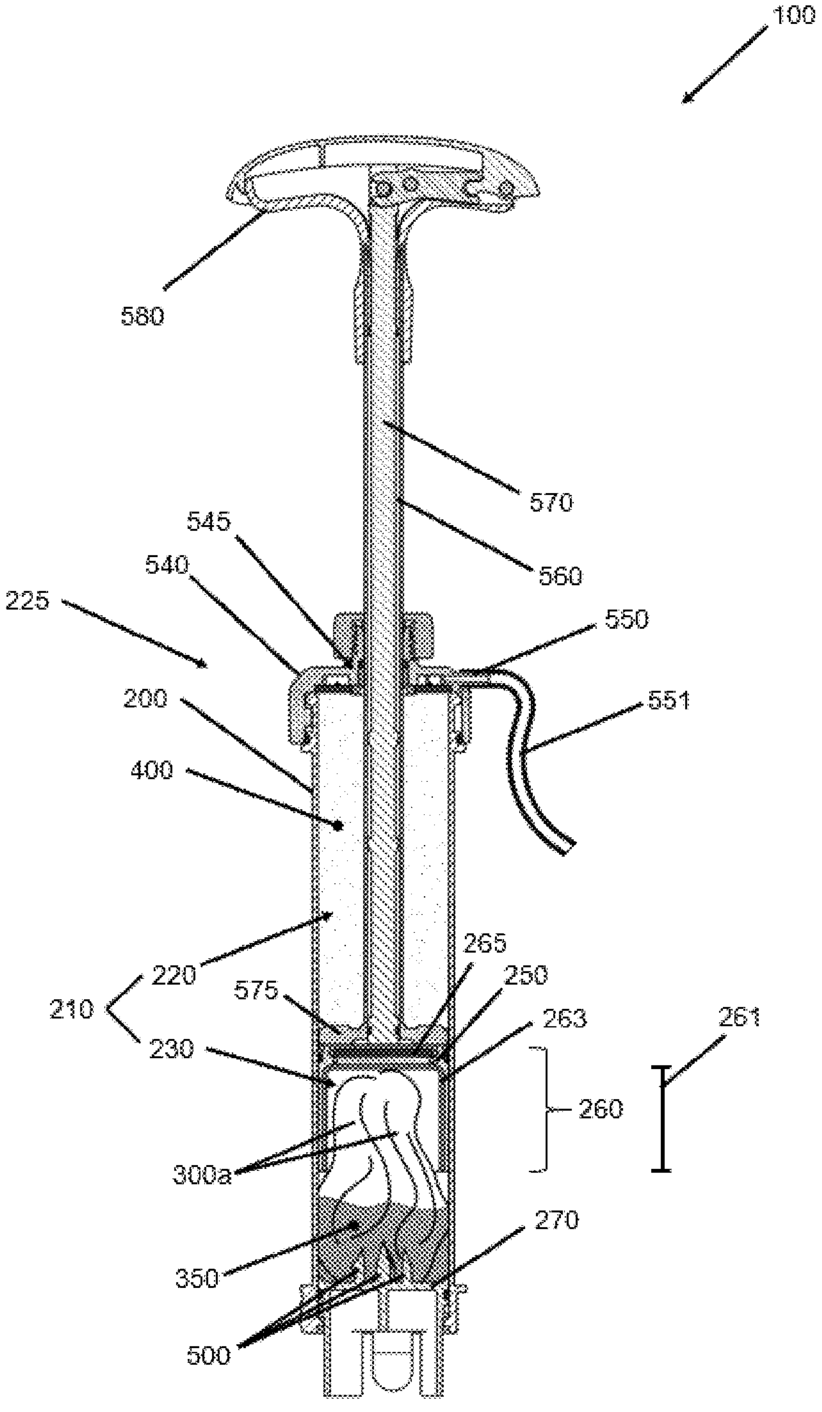

FIG. 2 shows the longitudinal section of the device 100 from FIG. 1, wherein, in FIG. 2, the dispensing plunger 250 and the feed plunger 270 are partially pushed together in comparison to FIG. 1. In order to make it easier to push together the dispensing plunger 250 and the feed plunger 270, this can take place by applying force to the handle 580 in the direction of the feed plunger 270. The handle 580 thereby transmits the applied force via the mixing rod 570 to the dispensing plunger 250.

Due to the partial pushing together of the dispensing plunger 250 and the feed plunger 270, the bags 300 of FIG. 1 have been pressed against opening means 500 in the form of mandrels arranged on the feed plunger 270, so that they are present in FIG. 2 as a fluidically opened bag 300*a*, and the monomer liquid 350 has flowed out into the distal part 230 of the interior space 210.

Figure 3:
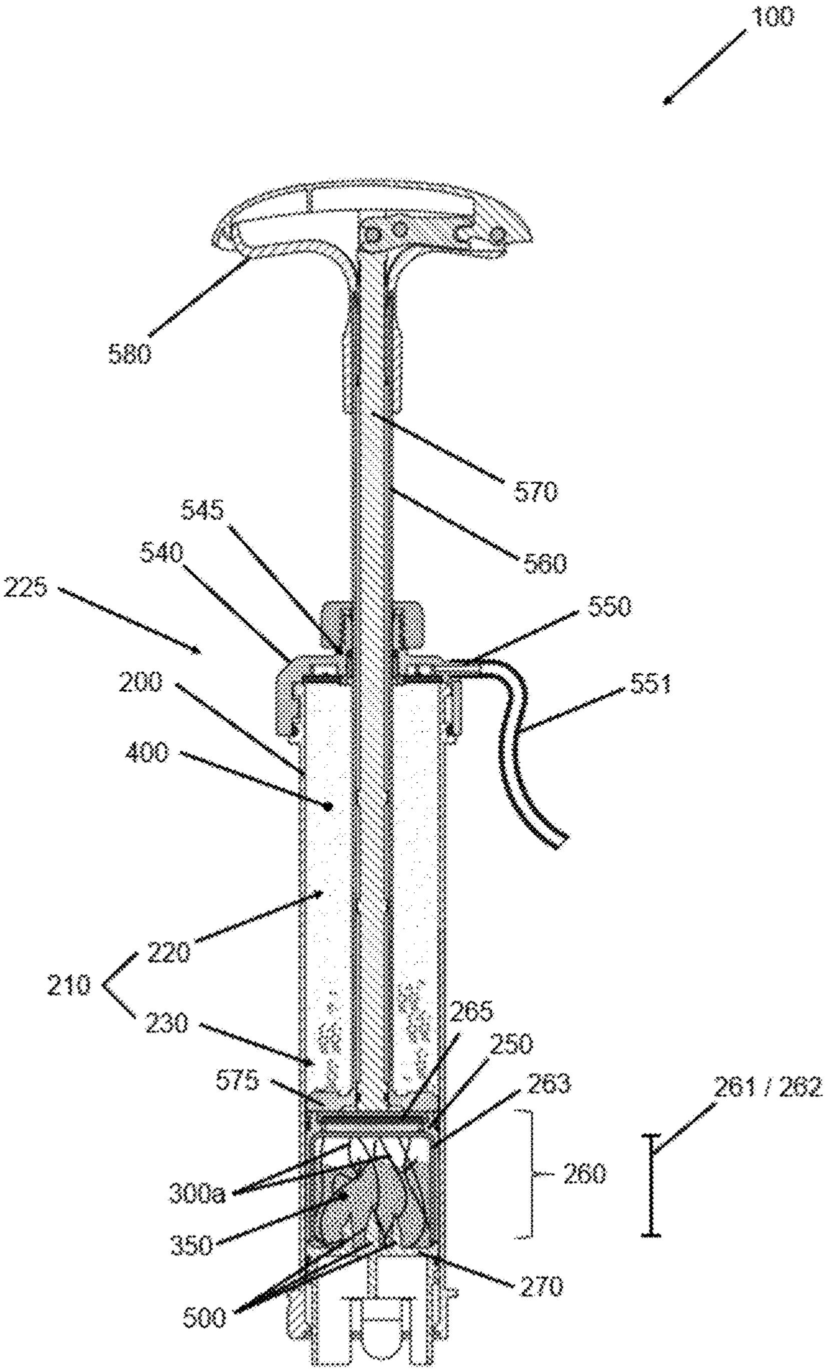

FIG. 3 shows the longitudinal section of the device 100 from FIGS. 1 and 2, wherein, in FIG. 3, the dispensing plunger 250 is displaced far enough in the direction of the feed plunger 270 for the two plungers 250, 270 to be spaced apart by the conduit 300. The conduit 260 is shaped to be dimensionally stable in the shown device 100; so, it is impossible to push together the dispensing plunger 250 and the feed plunger 270 any more without destroying the structural integrity of the conduit 260. The dispensing plunger 250 and the feed plunger 270 therefore have a plunger spacing 262 with respect to one another which substantially corresponds to the axial conduit length 261.

By pushing the dispensing plunger 250 and the feed plunger 270 together, a small amount of the monomer liquid 350 can be conveyed into the proximal part 220 of the interior space 210 (indicated by small droplets in the proximal part 220 of the interior space 210 proximal to the dispensing plunger 250). The opened bags 300*a* are pushed together in the shown position of the dispensing plunger 250, but not enough to require the user of the device 100 to exert a great amount of strength.

Figure 4:
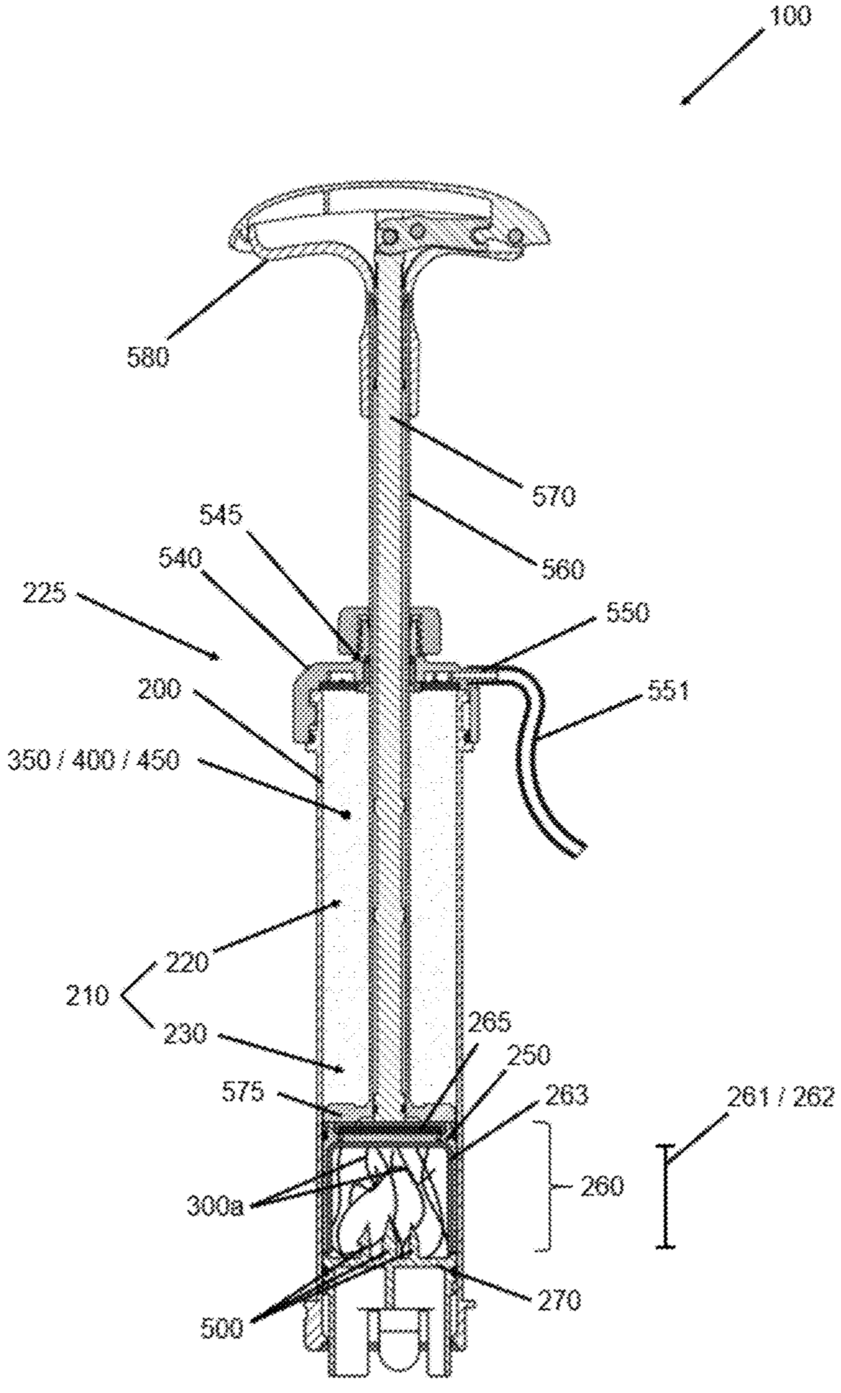

FIG. 4 shows the longitudinal section of the device 100 from FIGS. 1 through 3, wherein, in FIG. 4, basically all of the monomer liquid 350 from FIGS. 1 through 3 has been conveyed into the proximal part 220 of the interior space 210 through the conduit 260, and in particular the cylinder passages 263 of the conduit 260. In the proximal part 220 of the interior space 210, there is the monomer liquid 350, the bone cement powder 400, and a small amount of a bone cement paste 450 consisting of the monomer liquid 350 and the bone cement powder 400, by bringing the same into contact.

In order to convey the monomer liquid 350 from the distal part 230 into the proximal part 220 of the interior space 210 through the conduit 260, a vacuum was applied by means of a negative pressure source (not shown) in the proximal part 220 of the interior space 210 via the vacuum connector 550 and the hose 551.

Figure 5:
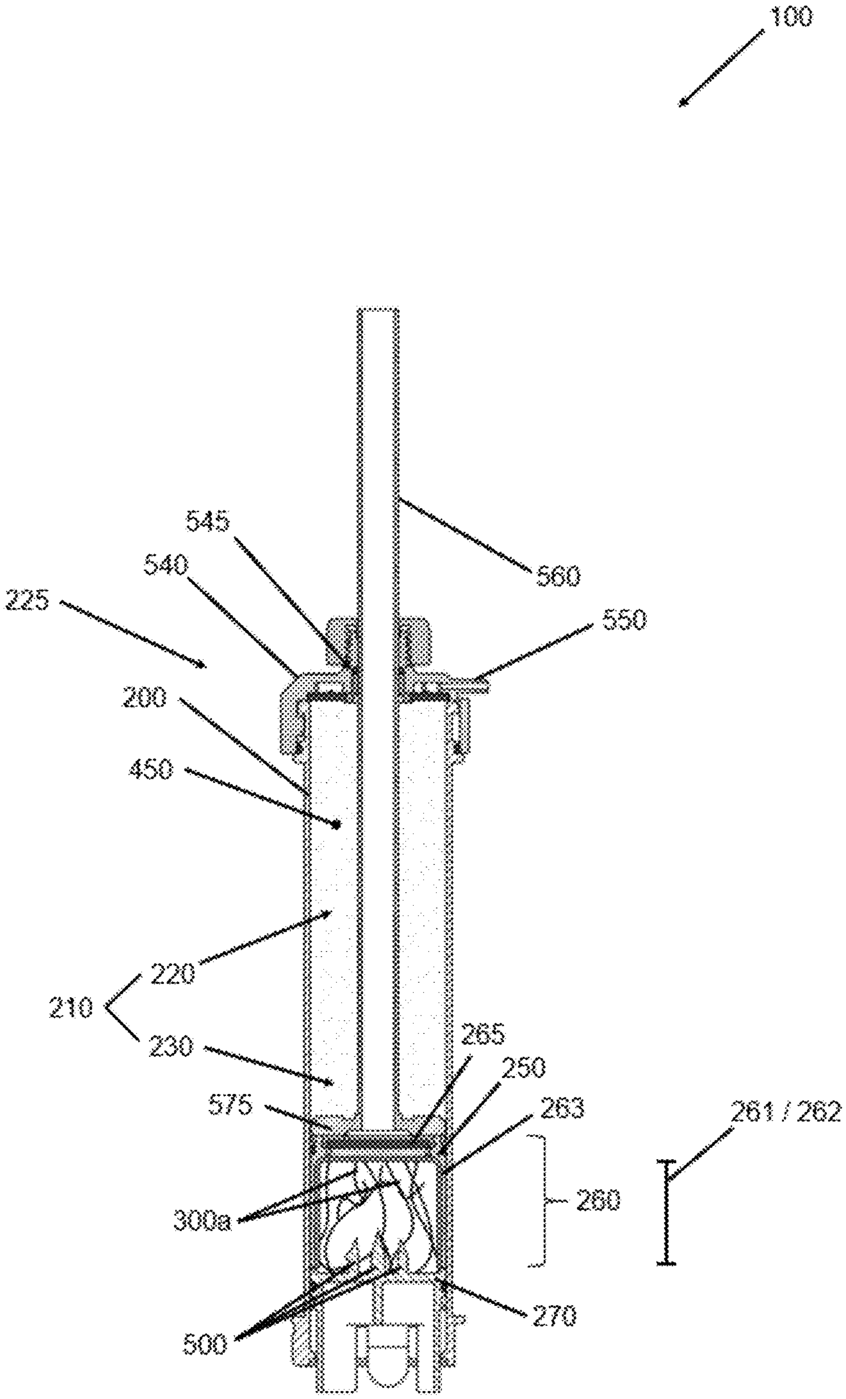

FIG. 5 shows the longitudinal section of the device 100 from FIGS. 1 through 4, wherein, in FIG. 5, basically all of the monomer liquid 350 and the bone cement powder 400 from the previous figures are converted into bone cement paste 450. For this purpose, the mixing tube 560, including the mixing disk 575, was repeatedly moved up and down axially in the proximal part 220 of the interior space 210 (not shown), and afterwards, the detachable handle 580 together with the mixing rod 570 were removed from the mixing tube 560. The starting components are preferably mixed under the influence of the negative pressure which was provided via the vacuum connector 550 for conveying the monomer liquid 350 into the proximal part 220 of the interior space. After mixing, the negative pressure is no longer necessary, such that the hose 551 has been removed.

Figure 6:
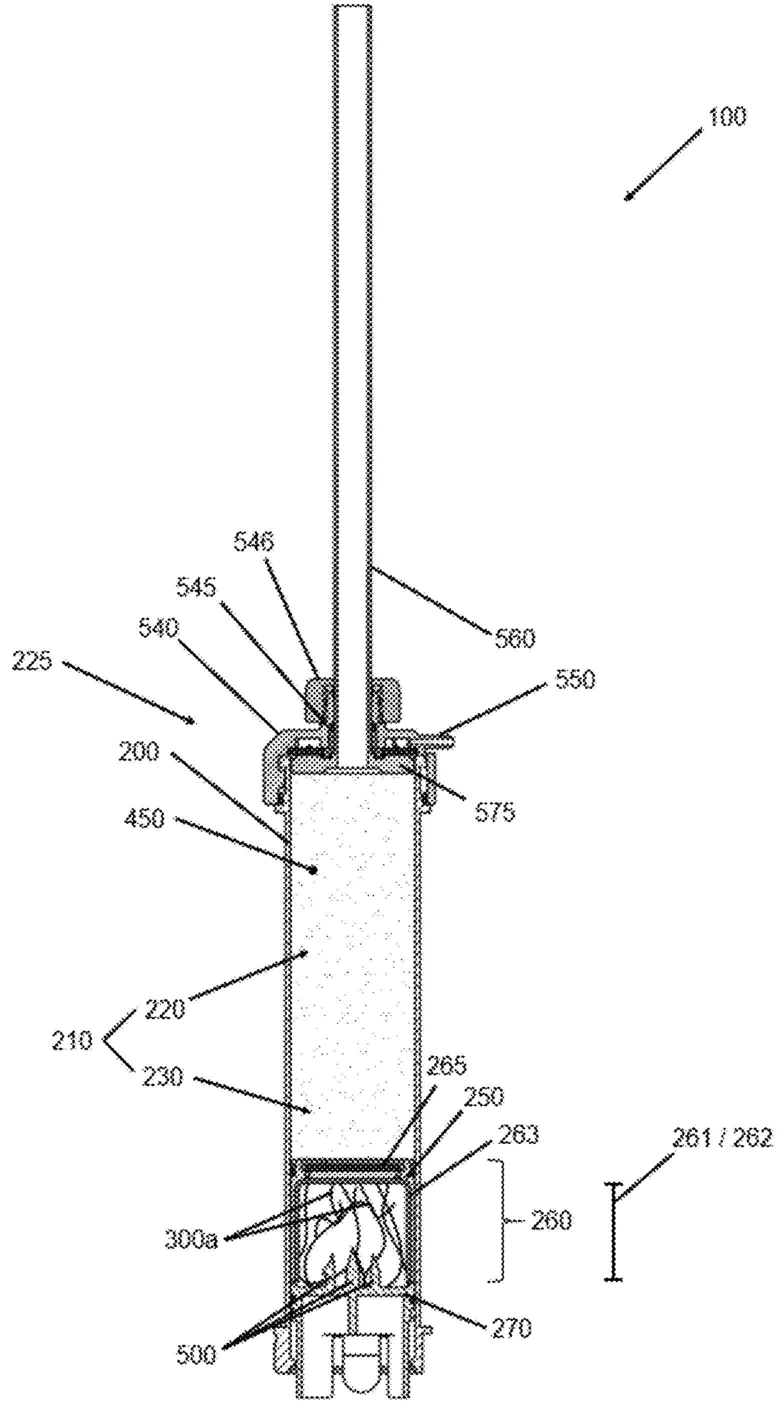

FIG. 6 shows the longitudinal section of the device 100 from FIGS. 1 through 5, wherein, in FIG. 6, the mixing tube 560 is pulled out of the proximal part 220 of the interior space 210 through the cartridge head passage 545 enough for the mixing disk 575 to rest distally against the cartridge head 540. After removal of the mixing rod 570 from the mixing tube 560 (cf. FIG. 5), the mixing tube 560 can therefore serve as a fluid-conducting dispensing snorkel for the provided bone cement paste 450. So that the mixing tube 560 is not unintentionally pushed back into the proximal part 220 of the interior space 210 when the bone cement paste 450 is discharged, it is reversibly fixed with a screw thread 546 in the cartridge head passage 545.

Figure 7:
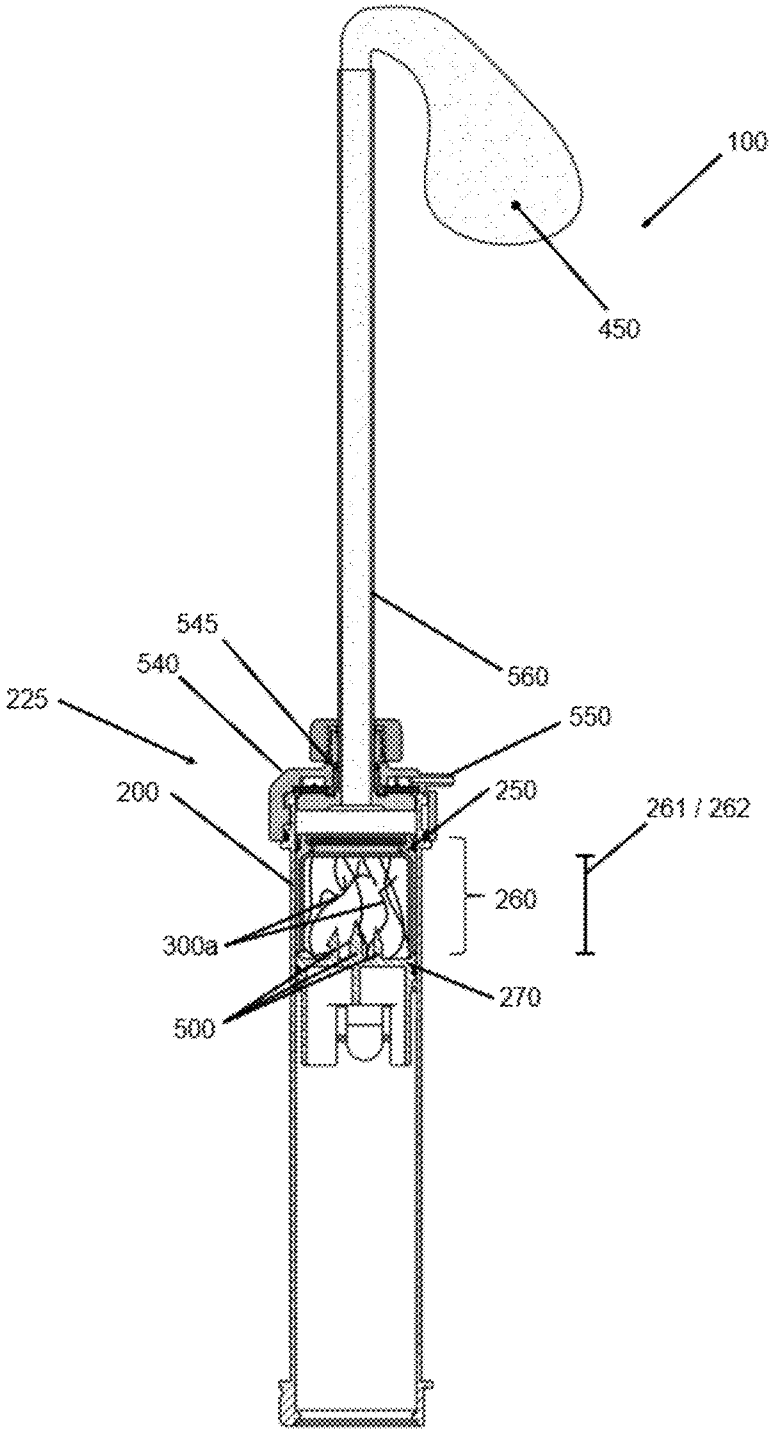

FIG. 7 shows the longitudinal section of the device 100 from FIGS. 1 through 6, wherein, in FIG. 7, the feed plunger 270, and therefore also the dispensing plunger 250, is displaced in the direction of the cartridge head 540 via the conduit 260. As a result, the provided bone cement paste 450 has been proportionately discharged from the device 100 from the proximal part 220 of the interior space 210 via the mixing tube 560. In order to facilitate the displacement of the feed plunger 270 for the user of the device 100, the feed plunger 270 can be connected to a dispensing aid—for example, a discharge gun (not shown). To this end, the feed plunger 270 is equipped with a delivery plunger connector on its side facing away from the dispensing plunger 250 in order to reversibly connect the feed plunger 270 to the dispensing aid.

Figure 8:
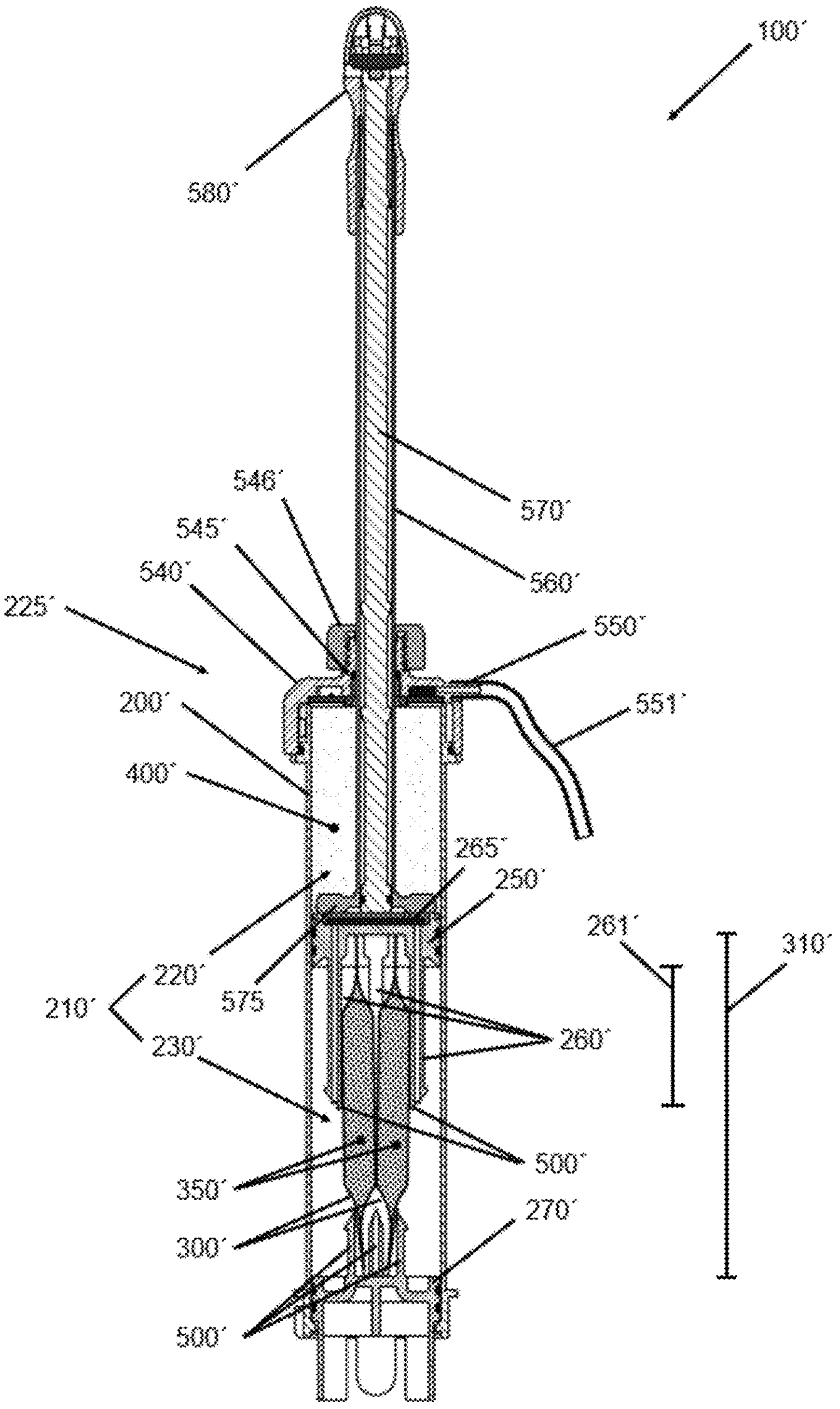

FIG. 8 shows a schematic longitudinal section of another exemplary embodiment of a device 100' for providing a bone cement paste from two starting components. The embodiment of the device 100' largely corresponds to the embodiment described above and shown in FIGS. 1 through 7, and therefore reference is made to the above description in order to avoid repetitions. Modifications to the embodiment shown in FIGS. 1 through 7 have the same reference signs, with an apostrophe.

The conduit 260' of the device 100' is designed in the form of four, uniformly distributed, dimensionally stable tubes (two of the tubes are in the drawing plane; one is located behind and one in front of the drawing plane) which have an axial conduit length 261' which corresponds approximately to one-half the bag length 310'. The tubes are each designed as a mandrel on a tube end facing the feed plunger 270 and therefore function as another opening means 500' beyond the opening means 500' arranged on the feed plunger 270', which additionally facilitates the fluidic opening of the bags 300'.

Figure 9:
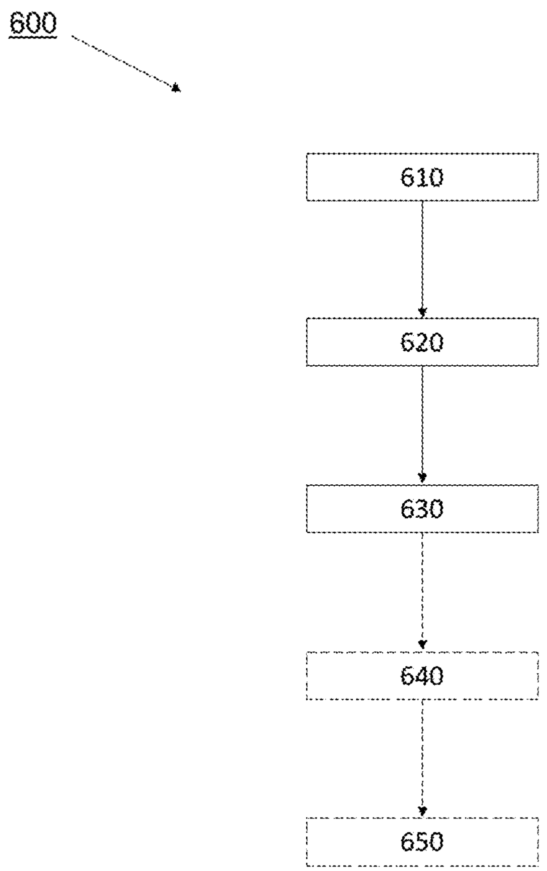

FIG. 9 shows a method 600 for providing a bone cement paste 450 from two starting components by means of one of the devices 100, 100 ' according to FIGS. 1 through 8, comprising the steps 610, 620, and 630, as well as preferably also the steps 640 and 650.

In a step 610, the dispensing plunger 250, 250' and the feed plunger 2270, 270' are pushed together, thereby reducing their distance from one another. Preferably, the dispensing plunger 250, 250' is moved in the direction of the feed plunger 270, 270', while the feed plunger 270, 270' remains at its original position within the interior space 210, 210'. In this way, more space remains in the proximal part 220, 220' of the interior space 210, 210' for later mixing the bone cement powder 400, 400' and the monomer liquid 350, 350', forming the bone cement paste 450.

By pushing together the two plungers 250, 250', 270, 270', the at least one bag 300, 300' is fluidically opened, and the monomer liquid 350, 350' flows into the distal part 230, 230' of the interior space 210, 210'.

In a step 620, the dispensing plunger 250, 250' and the feed plunger 270, 270' are pushed together more, wherein it is furthermore preferred that only the dispensing plunger 250, 250' move, until the conduit 260, 260' is arranged on the feed plunger 270, 270', and is preferably in contact with the feed plunger 270, 270'. In this position, the conduit 260, 260' spaces apart the two plungers 250, 250', 270, 270' from one another, and further pushing together is impossible without destroying the structural integrity of the conduit 260, 260'. By arranging the conduit 260, 260' on the feed plunger 270, 270', the monomer liquid 350, 350' can be received directly adjacently to the feed plunger 270, 270' into the conduit 260, 260' and conveyed through the conduit 260, 260' into the proximal part 220, 220' of the interior space 210, 210'. When the two plungers 250, 250', 270, 270' are pushed together, the at least one fluidically opened bag **300*a* is compressed. Since the conduit 260, 260' has an axial conduit length 261, 261' which corresponds to at least a quarter of the bag length 310, 310', essentially not all of the bag 300, 300' must be compressed completely to convey basically all of the monomer liquid 350, 350' into the proximal part 220, 220' of the interior space 210, 210'. This makes it easier to use the device 100, 100' and allows basically all of the monomer liquid 350, 350' to be conveyed into the bone cement powder 400, 400'**.

In a step 630, the monomer liquid 350, 350' is conveyed by applying negative pressure at the vacuum connector 550, 550' through the conduit 260, 260' into the proximal part 220, 220' of the interior space 210, 210'. Preferably, the negative pressure is applied only when the conduit 260, 260' is arranged on the feed plunger 270, 270'.

Upon beginning to convey the monomer liquid 350, 350', the bone cement paste 450 starts to form from the two starting components. In order to obtain a bone cement paste 450 that is as homogeneous as possible, it is preferable for the mixing of the starting components to be actively assisted by the user of the device 100, 100'.

For this purpose, it is preferred that, in an optional step 640, the monomer liquid 350, 350' be mixed with the bone cement powder 400, 400' by means of the mixing rod 570, 570' while applying a negative pressure, forming the bone cement paste 450. The mixing rod 570, 570' is preferably detachably connected to the mixing tube 560, 560' so that an axial movement of the mixing rod 570, 570' is directly transferred to the mixing tube 560, 560'. The mixing tube 560, 560' is preferably equipped with a mixing element—preferably in the form of a mixing disk 575, 575'—in order to facilitate mixing. Mixing while applying negative pressure reduces gas inclusions in the provided bone cement paste 450.

In order to apply the provided bone cement paste 450 from the device 100, 100' to a desired location, it is preferable, in an optional step 650, for the mixing rod 570, 570' to be detached from the mixing tube 560, 560'—preferably by removing the handle 580, 580'- and pulled out of the mixing tube 560, 560'. Before or after the removal of the mixing rod 570, 570' from the mixing tube 560, 560', the mixing tube 560, 560' is preferably pulled out of the cartridge head 540, 540' far enough so that the mixing tube 560, 560' can be used as a dispensing snorkel for the bone cement paste 450. By advancing the dispensing plunger 250, 250' in the direction of the cartridge head 540, 540', the bone cement paste 450 is discharged from the device through the mixing tube 560, 560'. Preferably, the advancing of the dispensing plunger 250, 250' in the direction of the cartridge head 540, 540' is triggered by advancing the feed plunger 270, 270' in the direction of the cartridge head 540, 540'—preferably with the assistance of a dispensing aid, such as for example a discharge gun. This makes it easier for the user to use the device 100.

REFERENCE SIGNS

100, 100' Device
200, 200' Hollow cylindrical cartridge
210, 210' Interior space of the cartridge
220, 220' Proximal part of the interior space
225, 225' Proximal interior space end
230, 230' Distal part of the interior space
250, 250' Dispensing plunger
260, 260' Conduit
261, 261' Axial conduit length
262 Plunger spacing
263 Cylinder passage
264 Hollow cylinder diameter
265, 265' Porous disk
270, 270' Feed plunger
300, 300' Bag
310, 310' Bag length
**300*a*** Opened bag
350, 350' Monomer liquid
400, 400' Bone cement powder
450 Bone cement paste
500, 500' Opening means
540, 540' Cartridge head
545, 545' Cartridge head passage
546, 546' Screw thread
550, 550' Vacuum connector
551, 551' Hose
560, 560' Mixing tube
570, 570' Mixing rod
575, 575 ' Mixing plate
580, 580' Handle
600 Method for providing a bone cement paste
610 Pushing together
620 Continued pushing together
630 Conveying
640 Mixing
650 Discharging

What is claimed is:

1. A device for providing a bone cement paste from two starting components, comprising a hollow cylindrical cartridge having an interior space, wherein, in a proximal part of the interior space, a bone cement powder is stored as the first starting component, and, in a distal part of the interior space, at least one bag is stored containing a monomer liquid as the second starting component, wherein the interior space is connectible at the proximal part of the interior space to a negative pressure source via a vacuum connector, wherein a dispensing plunger which is axially movable in the interior space is arranged between the bone cement powder and the at least one bag, and a feed plunger which is axially movable in the interior space is arranged on a side, axially opposite the dispensing plunger, of the at least one bag such that, when the dispensing plunger and the feed plunger are pushed together, the at least one bag is opened in a fluid-conducting manner and the monomer liquid can flow into the distal part of the interior space, wherein the proximal part and the distal part of the interior space are fluidly connected to one another via a conduit, wherein the conduit extends from the dispensing plunger into the distal part of the interior space with an axial conduit length corresponding to at least a quarter of a bag length of the bag, so that, when pushed together, the dispensing plunger and the feed plunger are spaced apart by the conduit by a plunger spacing corresponding to at least a quarter of the bag length; and wherein at least one opening means for opening the bag is arranged in the distal part of the interior space.

2. The device according to claim 1, wherein the conduit is substantially dimensionally stable.

3. The device according to claim 1, wherein the conduit is formed at least partially as a hollow cylinder with at least one cylinder passage extending axially in a hollow cylinder wall.

4. The device according to claim 1, wherein the conduit is formed at least partially as a tube and/or a hose.

5. The device according to claim 1, wherein the conduit has a fluid-conducting conduit inner diameter of 0.5 mm to 2 mm.

6. The device according to claim 1, wherein the opening means is formed as a mandrel and/or has at least one cutting edge.

7. The device according to claim 1, wherein a proximal interior space end, axially opposite the dispensing plunger, of the proximal portion of the interior space is fluidically closed with a cartridge head.

8. The device according to claim 7, wherein the vacuum connector is arranged on the cartridge head.

9. The device according to claim 7, wherein a mixing tube which can be displaced axially in the proximal part of the interior space is arranged in a cartridge head passage of the cartridge head.

10. The device according to claim 9, wherein a detachable mixing rod is arranged within the mixing tube.

11. A device for providing a bone cement paste from two starting components, comprising a hollow cylindrical cartridge having an interior space, wherein, in a proximal part of the interior space, a bone cement powder is stored as the first starting component, and, in a distal part of the interior space, at least one bag is stored containing a monomer liquid as the second starting component, wherein the interior space is connectible at the proximal part of the interior space to a negative pressure source via a vacuum connector, wherein a dispensing plunger which is axially movable in the interior space is arranged between the bone cement powder and the at least one bag, and a feed plunger which is axially movable in the interior space is arranged on a side axially opposite the discharge piston, of the at least one bag such that, when the dispensing plunger and the feed plunger are pushed together, the at least one bag, is opened in a fluid-conducting manner and the monomer liquid can flow into the distal part of the interior space, wherein the proximal part and the distal part of the interior space are fluidly connected to one another via a conduit, wherein the conduit extends from the dispensing plunger into the distal part of the interior space with an axial conduit length corresponding to at least a quarter of a bag length of the bag, so that, when pushed together, the dispensing plunger and the feed plunger are spaced apart by the conduit by a plunger spacing corresponding to at least a quarter of the bag length;

wherein the conduit is formed at least partially as a hollow cylinder with at least one cylinder passage extending axially in a hollow cylinder wall; and wherein the hollow cylinder has a hollow cylinder inner diameter which allows at least partial accommodation of the at least one bag.

12. A method for providing a bone cement paste from two starting components by means of the device of claim 1 for providing a bone cement paste from two starting components, the method comprising the following steps:

a. pushing together the dispensing plunger and feed plunger while opening the at least one bag;

b. continued pushing together of the feed plunger and dispensing plunger until the conduit is arranged on the feed plunger;

c. conveying the monomer liquid through the conduit into the proximal part of the interior space by applying a negative pressure at the vacuum connector.

13. The method according to claim 12, by means of a device according the detachable mixing rod is arranged within the mixing tube, wherein, in a step d., the bone cement powder and the monomer liquid in the proximal part of the interior space are mixed by means of the mixing rod with applied negative pressure while providing the bone cement paste.

14. The method according to claim 13, wherein, in a step e., the mixing rod is detached from the mixing tube, the mixing rod is pulled out of the mixing tube, and the mixed bone cement paste is discharged from the proximal part of the interior space through the mixing tube from the device by advancing the dispensing plunger in the direction of the cartridge head.

* * * * *